United States Patent

Priest et al.

Patent Number: 5,824,491
Date of Patent: Oct. 20, 1998

[54] DRY REAGENT TEST STRIP COMPRISING BENZIDINE DYE PRECURSOR AND ANTIPYRINE COMPOUND

[75] Inventors: John Hedger Priest, Everett; Eric Michael Nelson, Redmond, both of Wash.

[73] Assignee: Mercury Diagnostics, Inc., Scotts Valley, Calif.

[21] Appl. No.: 649,777

[22] Filed: May 17, 1996

[51] Int. Cl.[6] .............................. C12Q 1/54; C12Q 1/26; C12Q 1/28; G01N 33/53

[52] U.S. Cl. ........................... 435/28; 435/14; 435/25; 435/970; 436/63; 548/360.7; 534/822

[58] Field of Search .................... 435/14, 25, 28, 435/975, 970; 422/56, 57; 548/360.7; 534/822

[56] References Cited

U.S. PATENT DOCUMENTS

| | | | |
|---|---|---|---|
| 3,607,093 | 9/1971 | Stone | 23/253 |
| 3,802,842 | 4/1974 | Lange et al. | 23/253 TP |
| 3,999,158 | 12/1976 | Rae | 337/360 |
| 4,042,335 | 8/1977 | Clément | 23/253 TP |
| 4,061,468 | 12/1977 | Lange et al. | 23/253 TP |
| 4,066,403 | 1/1978 | Bruschi | 23/230 B |
| 4,101,381 | 7/1978 | Klose et al. | 195/99 |
| 4,110,079 | 8/1978 | Schaeffer et al. | 23/253 TP |
| 4,127,499 | 11/1978 | Chen et al. | 252/301.17 |
| 4,144,306 | 3/1979 | Fugueras | 422/56 |
| 4,166,093 | 8/1979 | Smith-Lewis et al. | 422/56 |
| 4,168,205 | 9/1979 | Danninger et al. | 435/10 |
| 4,258,001 | 3/1981 | Pierce et al. | 422/56 |
| 4,279,993 | 7/1981 | Magers et al. | 435/14 |
| 4,290,773 | 9/1981 | Magers et al. | 23/230 B |
| 4,318,984 | 3/1982 | Magers et al. | 435/14 |
| 4,339,242 | 7/1982 | Magers et al. | 23/230 B |
| 4,339,243 | 7/1982 | Magers et al. | 23/230 B |
| 4,340,392 | 7/1982 | Magers et al. | 23/230 B |
| 4,340,394 | 7/1982 | Magers et al. | 23/230 B |
| 4,340,395 | 7/1982 | Magers et al. | 23/230 B |
| 4,357,363 | 11/1982 | Pierce et al. | 427/2 |
| 4,380,585 | 4/1983 | Magers et al. | 436/66 |
| 4,381,921 | 5/1983 | Pierce et al. | 436/535 |
| 4,385,114 | 5/1983 | Güthlein et al. | 435/28 |
| 4,490,465 | 12/1984 | Limbach et al. | 435/14 |
| 4,729,950 | 3/1988 | Kricka et al. | 435/28 |
| 4,814,142 | 3/1989 | Gleisner | 422/56 |
| 4,824,639 | 4/1989 | Hildenbrand et al. | 422/56 |
| 5,173,261 | 12/1992 | Krause et al. | 422/58 |
| 5,183,742 | 2/1993 | Omoto et al. | 435/14 |
| 5,243,516 | 9/1993 | White | 364/413.07 |
| 5,306,623 | 4/1994 | Kiser et al. | 435/14 |
| 5,418,142 | 5/1995 | Kiser et al. | 435/14 |
| 5,520,883 | 5/1996 | Charlton et al. | 422/56 |
| 5,556,761 | 9/1996 | Phillips | 435/14 |

FOREIGN PATENT DOCUMENTS

| | | |
|---|---|---|
| 0 243 126 | 10/1987 | European Pat. Off. . |
| 3506365 | 8/1985 | Germany . |
| 4343082 | 6/1995 | Germany . |
| 46443 | 10/1988 | Hungary . |

*Primary Examiner*—Louise N. Leary
*Attorney, Agent, or Firm*—Burns, Doane, Swecker & Mathis

[57] ABSTRACT

A dry reagent test strip for determining the concentration of an analyte in a liquid sample is described. The test strip has a matrix containing reagent detection chemistry, which includes an oxidase enzyme that can utilize the analyte as a substrate forming hydrogen peroxide, a benzidine dye precursor, a peroxidase enzyme, and an antipyrine compound. The addition of an antipyrine compound to the reagent detection chemistry provides a standard concentration graph which is substantially linear in a desired range of analyte concentration. The precision and accuracy of reading the test strip are enhanced.

14 Claims, 7 Drawing Sheets

FIG_1

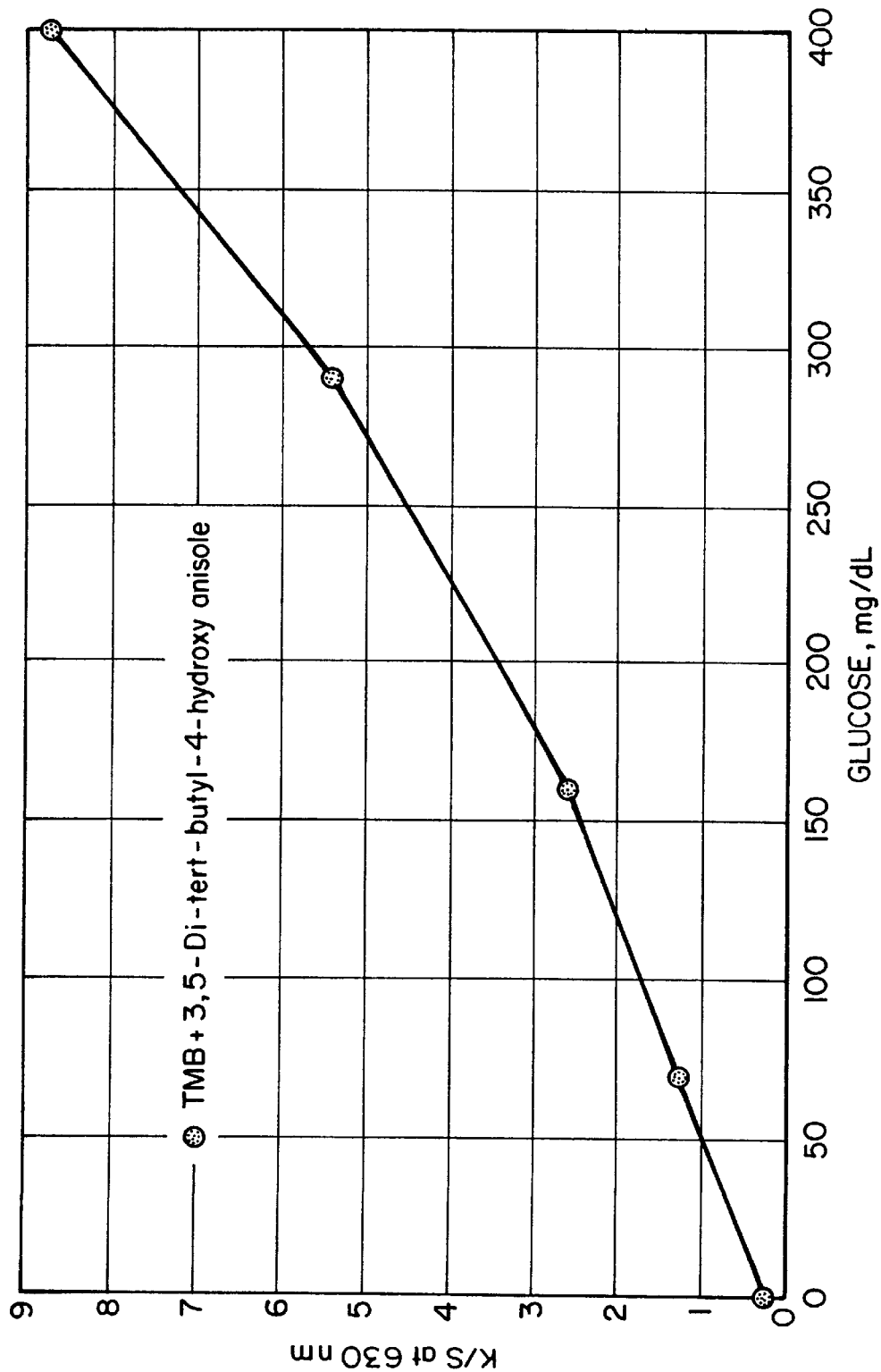
FIG_3

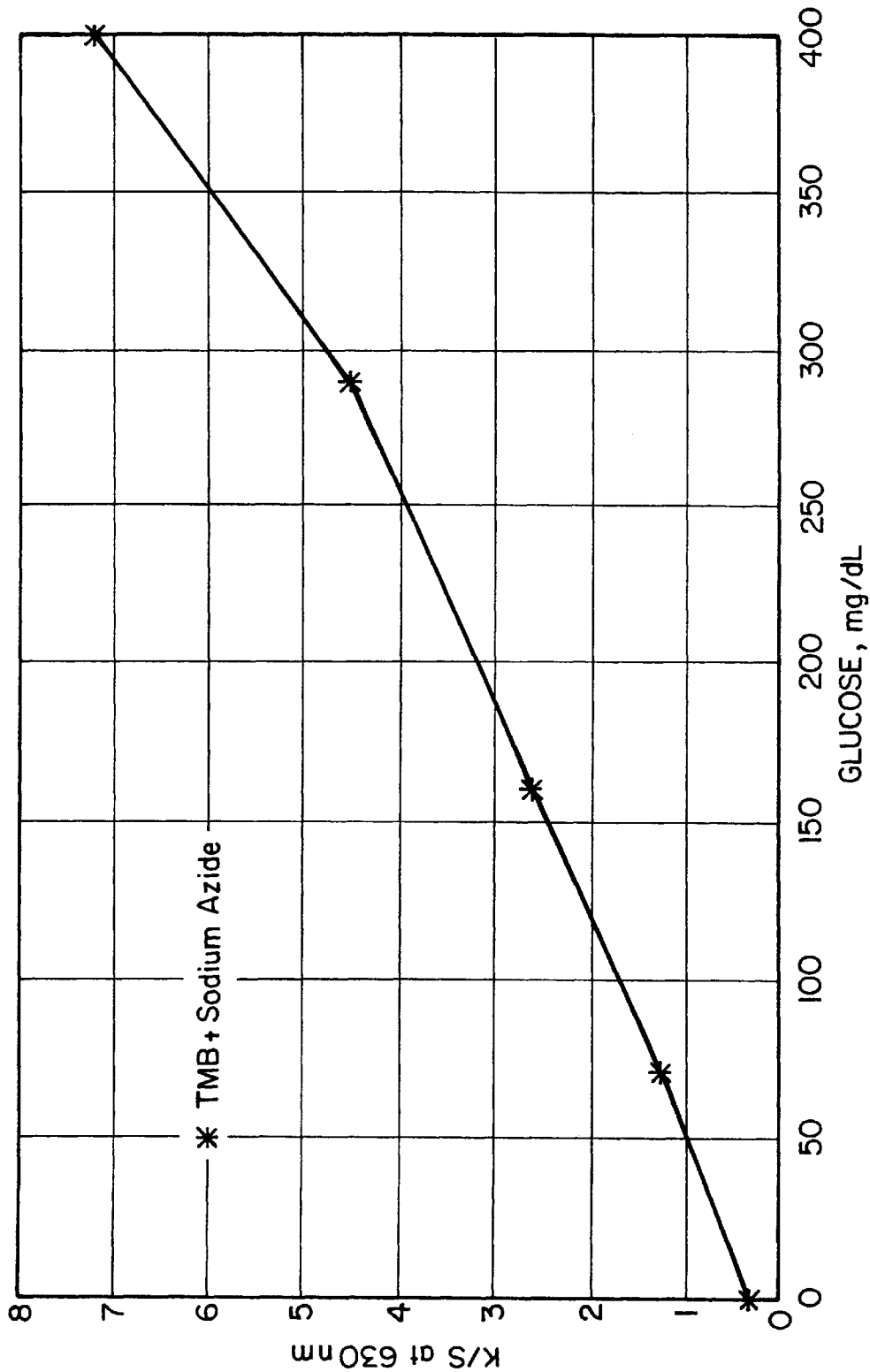
FIG_4

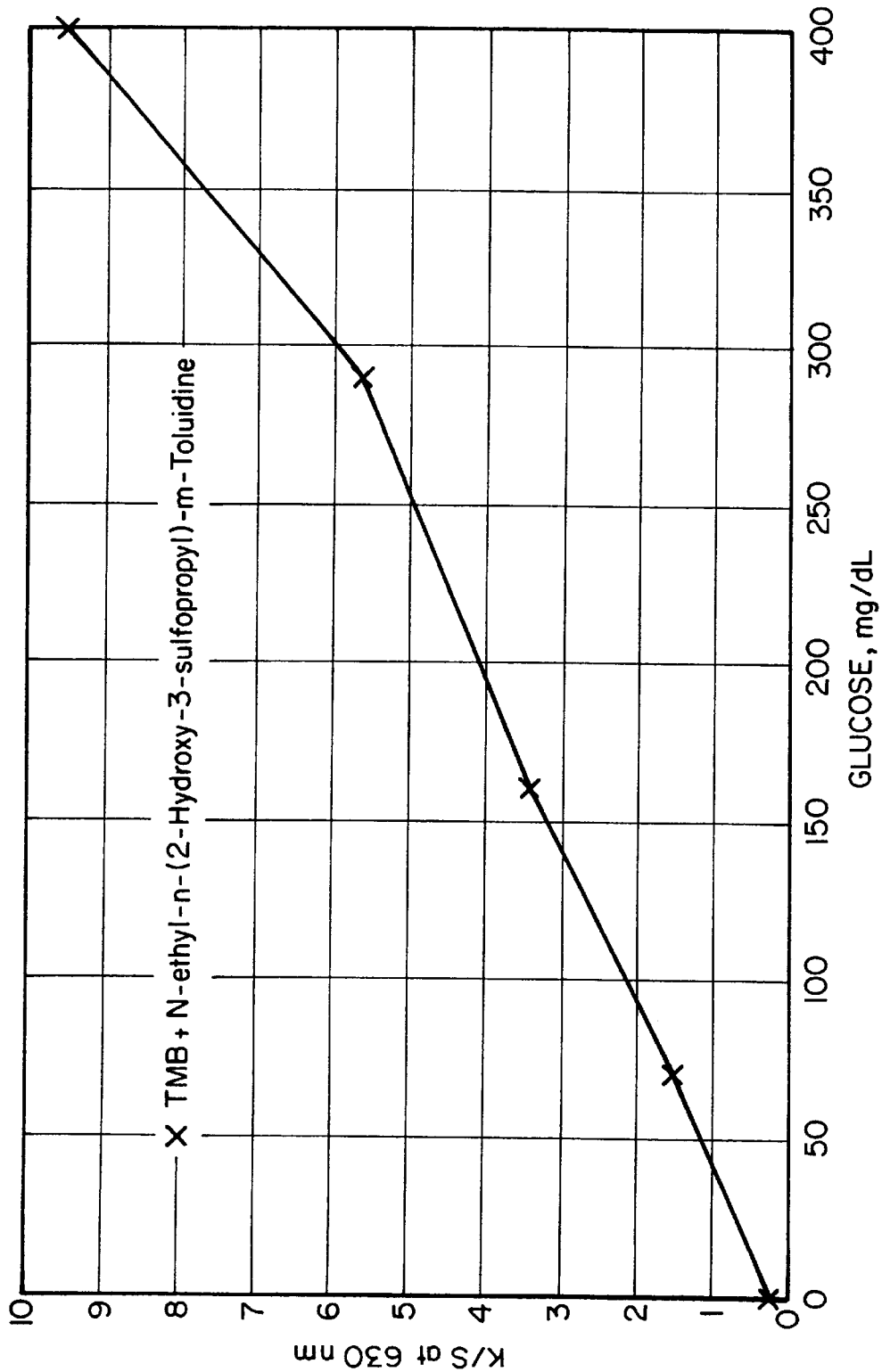
FIG_5

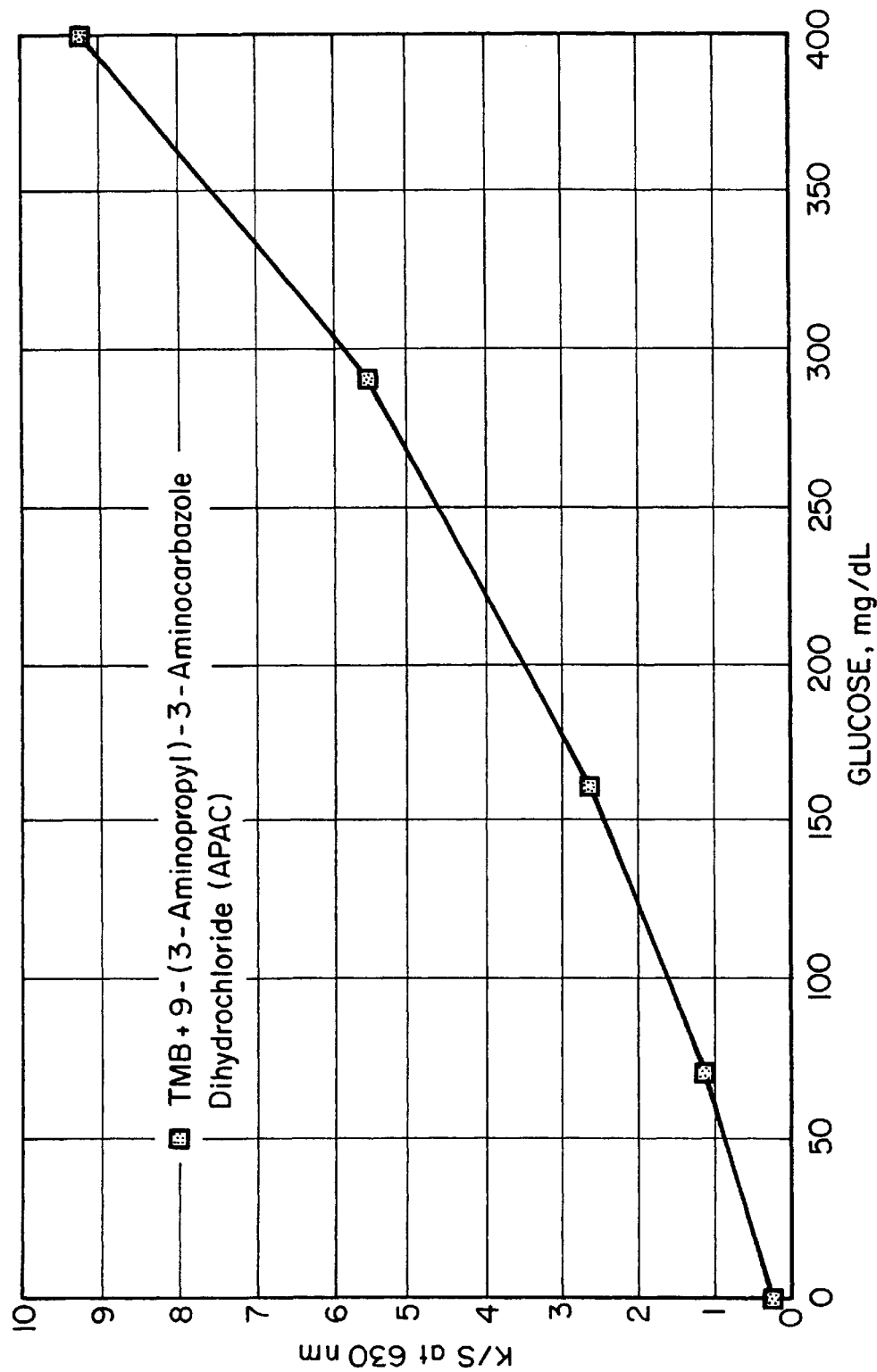

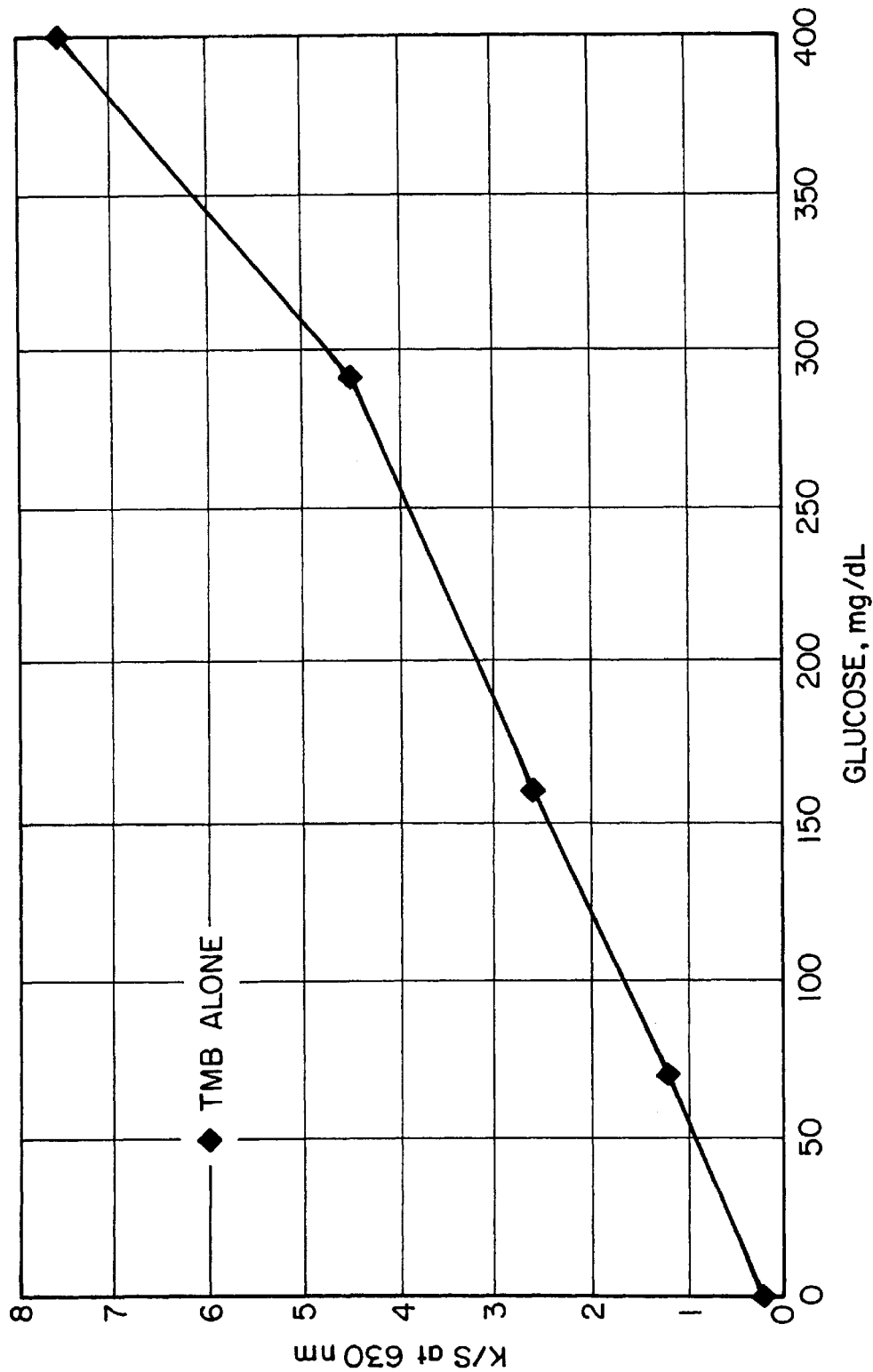
FIG_7

DRY REAGENT TEST STRIP COMPRISING BENZIDINE DYE PRECURSOR AND ANTIPYRINE COMPOUND

FEILD OF THE INVENTION

The present invention relates to dry reagent test strips useful for detecting analytes in body fluids, and particularly to stable test strips comprising a matrix containing reagent detection chemistry including a benzidine type dye precursor and an antipyrine compound. Typically, the test strip is used to test for the presence of a specific analyte, such as blood glucose.

BACKGROUND OF THE INVENTION

The analysis of liquid test samples by use of dry reagent test strips finds utility in a variety of areas ranging from the medical field to food industries. Depending upon the reagent (s) present in the test strip, the strip can be used for detecting and diagnosing a variety of different conditions ranging, for example, from diabetes to pregnancy. In the food industry, the presence of, for example, maltose can be monitored in brewing where starch is converted to sugars such as maltose prior to fermentation to assure high yield from the grain starting materials.

Typically, test strips take advantage of a reaction between the substance to be tested and a reagent system present in the test strip. Generally, the test strip will take advantage of a color change, i.e., a change in the wavelength absorbed or reflected by dye formed by the reagent system used. See, U.S. Pat. No. 3,802,842, U.S. Pat. No. 4,061,468 and U.S. Pat. No. 4,490,465. In testing for the presence of an analyte such as glucose in a bodily fluid, test strips commonly take advantage of an oxidation/reduction reaction which occurs using an oxidase/peroxidase detection chemistry. The test strip is exposed to a drop of the fluid to be tested for a suitable period of time and there will be a color change if the analyte (glucose) is present. Typically, the intensity of this change is proportional to the concentration of analyte in the sample. The color of the test strip is then compared to a known standard which enables one to determine the amount of analyte present in the sample. This determination can be made by a visual check or by an instrument, such as a reflectance spectrophotometer at a selected wavelength such as a blood glucose (or other electronic photometer) meter, for a more accurate determination of concentration in the sample.

For example, in determining the concentration of glucose present in a sample, the color change in the test strip is measured by a photometer or a blood glucose meter. If the determination of blood glucose is made by a blood glucose meter, then the meter will automatically convert a given amount of color intensity in the strip into a glucose concentration reading of the blood sample. For any given chemistry in a strip there will be a characteristic curve of light absorbance in the reflectance mode versus glucose concentration. This characteristic curve may vary depending on a number of physical chemical characteristics in the test strip, but in general it will be linear at low concentrations of glucose and deviate from linearity as the glucose concentration, and hence the strip color, is increased. A graph (or calibration curve) is used to represent the correspondence between absorbance and glucose concentration. A standard, or control, graph is used for comparison to measurements taken with the test sample, producing a reading of glucose concentration. It is desirable that the relationship be as linear as possible in the desired range of glucose concentration for the purposes of precision and accuracy in determining the glucose concentration in a test sample. For example, for blood glucose testing, the normal range for healthy non-diabetic individuals is about 60–120 mg/dl. Even for diabetics, it is desirable that they keep their blood glucose above about 50 mg/dl and below about 160 mg/dl. Therefore, it is desirable for the graph to be as linear as possible over the range of 50 to 160 mg/dl, in addition to having a suitable slope, to provide more accurate and precise readings.

Various additives have been tried to alter the characteristic curve produced by benzidine dyes formed in dry reagent test strips using the oxidase/peroxidase reagent detection chemistry to improve the linearity of absorbance versus analyte concentration. Various reducing agents, such as 3-hydroxy-2,4,6-triiodo-benzoic acid, 3,5-di-tert-butyl-4-hydroxyanisole ("BHA"), sodium azide, N-ethyl-N-sulfopropyl-m-tolidine and 9-(3-aminopropyl)-3-amino carbazole, were tried. However, none affected the linearity of the graph in the desired range by any appreciable amount.

Thus, compositions and methods for providing improved linearity of absorbance versus analyte concentration are desired.

SUMMARY OF THE INVENTION

Test strips in accord with the present invention provide a more linear graph of absorbance versus analyte concentration when using reaction detection chemistry comprising a benzidine or tolidine dye precursor in an oxidase/peroxidase dry reagent detection system. Thus, in accord with the invention, a test strip comprises a matrix containing reagent detection chemicals, wherein the reagent detection chemicals include oxidase, peroxidase, a benzidine dye precursor and an antipyrine compound.

For purposes of the present invention, the term benzidine type dye precursor is meant to include benzidine, tolidine and dye forming derivatives and salts thereof. Particularly useful dye forming derivatives of benzidine are tetraalkyl benzidines. Also, for purposes of this invention, the term antipyrine compound is meant to include antipyrine and derivatives and salts thereof. Particularly useful derivatives of antipyrine are the aminoantipyrines, e.g., 4-aminoantipyrine.

In use, when contacted with a liquid test sample containing an analyte such as glucose, the test strips of the invention provide a color having an intensity proportional to the concentration of the analyte, wherein the relationship between concentration of the analyte and the intensity of the color is surprisingly more linear in a predetermined desirable range than test strips without the antipyrine compound. The addition of an antipyrine compound provides a standard curve of analyte concentration versus reflectance which is substantially linear in the desired range. This enhances the precision and accuracy of the reading.

The nature of the mechanism by which the antipyrine compound acts is not known. Although the antipyrine compound can act as a reducing agent in the reaction, other reducing agents such as, for example, 3-hydroxy-2,4,6-triiodo benzoic acid, 3,5-di-tert-butyl-4-hydroxyanisole, sodium azide, N-ethyl-N-sulfopropyl-m-tolidine and 9-(3-aminopropyl)-3-amino carbazole, were tried in comparable amounts in glucose test strips in place of an antipyrine compound. However, none of those reducing agents affected the linearity of the graph in the selected range by any appreciable amount. Thus, the effect of antipyrine compounds in test strips containing benzidine dye precursors is surprising.

BRIEF DESCRIPTION OF THE DRAWINGS

FIG. 3 is a graph illustrating a calibration curve of reflection reading versus glucose concentration for the test strip of Example 3.

FIG. 4 is a graph illustrating a calibration curve of reflection reading versus glucose concentration for the test strip of Example 4.

FIG. 5 is a graph illustrating a calibration curve of reflection reading versus glucose concentration for the test strip of Example 5.

FIG. 6 is a graph illustrating a calibration curve of reflection reading versus glucose concentration for the test strip of Example 6.

FIG. 7 is a graph illustrating a calibration curve of reflection reading versus glucose concentration for the test strip of Example 7.

DETAILED DESCRIPTION OF THE INVENTION

Figure 1:
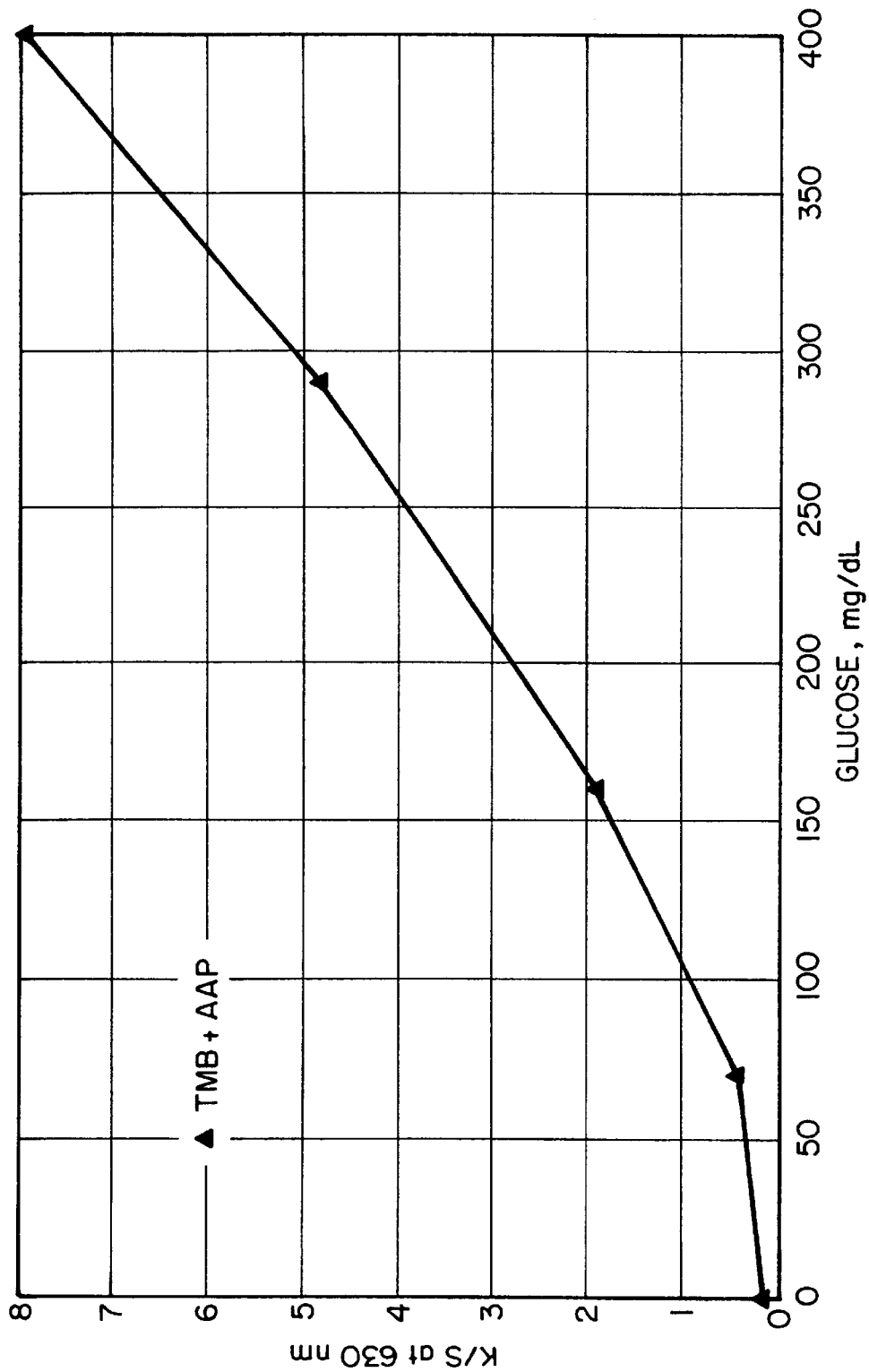
FIG. 1 is a graph illustrating a calibration curve of reflection reading versus glucose concentration for the test strip of Example 1.
Figure 2:
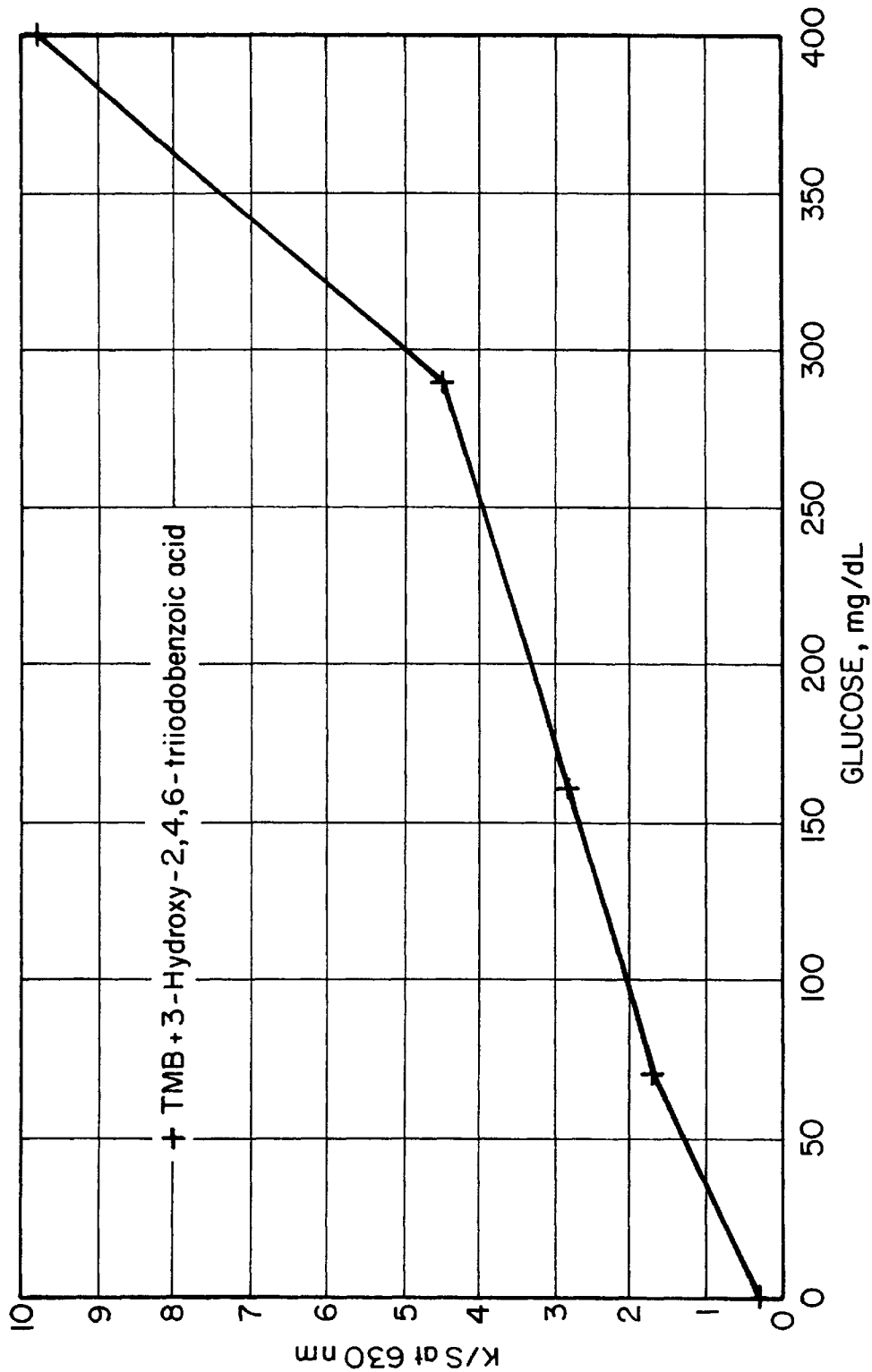
FIG. 2 is a graph illustrating a calibration curve of reflection reading versus glucose concentration for the test strip of Example 2.

Test strips in accord with the present invention comprise a matrix containing reagent detection chemistry. When the matrix is not self-supporting, the test strips typically comprise a support layer having the matrix thereon. Preferably, the support is essentially insoluble during the test and maintains structural integrity when exposed to the material to be tested. Materials which can be used as such a support include glass fibers, plastics, hardened gelatin, agarose, various organic polymers such as polypropylene, polyvinylchloride, polystyrene, etc. Preferably, the support is a solid non-absorbent material.

In one embodiment of a test strip wherein the sample is applied and the reflectance reading is made from the same surface of the test strip, the support has a matte finish on the side adjacent the reagent layer. When the colorimetric change is read visually or by reflectance spectrophotometry, the support is preferably highly reflective to increase color contrast. Such a support includes the above materials as well as suitably finished metal foils. When the color change is read by transmission spectrophotometry, a transparent support is preferred.

The matrix typically is carried on the support layer. The matrix can be a preformed porous membrane on which reagent detection chemistry is coated or the reagent chemistry and matrix material can be coated on the support, forming the matrix in situ. The matrix itself can be a single layer or multiple layers. For instance, a single permeable membrane, in which detection reagents are incorporated, is described in U.S. Pat. No. 3,607,093. Also, it is possible to combine a reagent layer optionally with various additional functional layers or membranes, as exemplified by the reagent layer, reflection layer and undercoating layer described in U.S. Pat. 3,999,158, the radiation blocking layer described in U.S. Pat. 4,042,335, the barrier layer described in U.S. Pat. 4,066,403, the registration layer described in U.S. Pat. 4,144,306, the migration inhibition layer described in U.S. Pat. 4,166,093, the scintillation layer described in U.S. Pat. 4,127,499, the scavenging layer described in Japanese Patent Publication 90859/1980, the destructive pod-like member described in U.S. Pat. 4,110,079, the dialyzed latex polymeric layer described in U.S. Pat. 4,814,142 and the like, the disclosures of which are hereby incorporated by reference.

The methods of preparation of the aforesaid layers and the methods for incorporation of the aforesaid layers into test strips of the present invention can be the same or similar to those methods described in the above patents. Materials useful in the preparation of such reagent layers and other layers are also disclosed in the above mentioned patents.

The reagent layer of the present invention conveniently contains one or more reagent compositions to provide a reagent detection system for detecting a pre-determined analyte, i.e., a substance or component in a liquid test sample, e.g., a body fluid. On interaction with the substance sought to be detected (analyte) or a reaction product or decomposition product of the analyte by the reagent detection system incorporated in the reagent layer, a detectable change is caused to occur. Preferably, the detectable change is a visible change such as, for example, formation of a colored compound.

As used herein, the expression "interaction" means chemical activity, catalytic activity (formation of enzyme-substrate conjugate formation), immunogenic activity (antigen-antibody reaction) and any other form of electrical, chemical or physical action. Through such chemical, electrical or physical actions, detectable changes are formed or provided in the test strip as is well known in the analytical field. By the aforesaid changes, there can be determined directly or indirectly the presence and/or concentration of the substance in the test sample.

The detectable change preferably is detected by radiation measurement. The radiation measurement refers to detection by use of an electromagnetic radiation measurement such as colorimetric measurement, fluorescence measurement or emission measurement.

In the present invention, the detectable compound is a benzidine or tolidine dye, which is formed when the test sample containing the analyte reacts with the detection reagents. The detection reagents in the test strips of the present invention include an oxidase/peroxidase enzyme system, a benzidine type dye precursor and an antipyrine compound. The benzidine type dye precursor is a compound typically comprising a $H_2N-C_6H_5$ moiety; tolidine has one such moiety and benzidine has two such moieties connected by deletion of hydrogen atoms, i.e., $H_2N-C_6H_4C_6H_4-NH_2$. Commonly available and preferred benzidine type dyes include those formed by o-tolidine, dianisidine, diaminobenzidine, benzidine and tetramethylbenzidine. Other benzidine dye precursors such as tetraalkylbenzidines described in U.S. Pat. No. 4,385,114 are also useful in the practice of the present invention. Useful salts include the hydrochloride salts of such dye precursors.

When the analyte contacts the oxidase enzyme, hydrogen peroxide is formed. The hydrogen peroxide reacts with the benzidine dye precursor in the presence of a peroxidase enzyme to form a compound or dye that absorbs radiation, typically visible light, at a wave length not absorbed by the dye precursor. The amount of dye formed is proportional to the amount of analyte in the test sample and is typically measured by a spectrophotometer or photometer, as is well known in this art.

By using the appropriate oxidase, one can test for a wide variety of different substances, e.g., glucose, alcohol, etc. For example, when testing for the presence of glucose in accord with the present invention, the reagent layer typically contains a benzidine dye precursor which, for example, detects the presence of hydrogen peroxide formed by the reaction of the glucose in the presence of a glucose oxidase and horseradish peroxidase (HRP). As a result of this reaction, the indicator agent, i.e., the benzidine dye precursor, changes color and the color change is proportional to the amount of glucose present. Other color indicator systems which can be used are well known to a person of ordinary skill in the art.

The amount of glucose present in the fluid is determined by comparing the results of the assay taken with known standards. The concentration is obtained by reading the test strip with, e.g., a reflectance spectrophotometer or photometer, and comparing the reading with a standard graph (or calibration curve) prepared by using standard glucose solutions of known concentrations. Data for the calibration curves can be stored in a meter and comparisons made electronically to provide the glucose concentration in the test sample on a digital display.

Preferably, the calibration curves are substantially linear over the range of concentration of interest for the particular analyte, increasing the accuracy and precision in the reading. It is also important for the calibration curves for the test strips to be stable during storage on the shelf over the commercial life of the test strip. For glucose testing, it is desirable that the calibration curve be linear in the 60–160 mg/ml range. This is the range of glucose levels in the majority of test subjects.

The addition of an antipyrine compound to test strip detection reagent formulations containing a benzidine dye precursor has been found to substantially improve the linearity of the calibration curve. Preferably, the antipyrine compound is an aminoantipyrine, and more preferably 4-aminoantipyrine. The antipyrine compound is present in the formulation in an amount from about 0.1% to about 30% by weight of the dye precursor, preferably from about 1% to about 5%.

The detection reagent formulations can also contain additional reagents useful for coating, stabilizing the enzymes, preventing picture framing of the dye formed by the reaction, etc. As such, buffering agents, surfactants, proteins, natural and synthetic polymers, and the like, known to provide the desired effect can be used, as is well known in the art.

The following examples are provided to further illustrate the present invention. Preferred embodiments are described and pertinent performance data is presented and illustrated. These examples are meant to be illustrative only and are in no way intended to limit the scope of the invention described and claimed herein.

A series of test strips were prepared using an enzyme solution consisting of:

| | |
|---|---|
| Water | 3.63 mL |
| 6% Gantrez | 0.500 mL |
| 1.66M citrate | 0.500 mL |
| Citrate Buffer, pH 4.726 | 0.500 mL |
| Glucose Oxidase (8090 I.U.) | 0.240 mL |
| HRP (7683 I.U.) | 0.040 mL |

A dye solution for the test strips contained:

| | |
|---|---|
| o-Tolidine HCl | 198 mg |
| 2-methoxy ethanol | 10.0 mL |
| 50% Byco-O* | 6.169 g |

| | |
|---|---|
| additive | (see below) |

The amount of additive in each formulation was calculated to be the molar equivalent to the amount of 4-aminoantipyrine used in Example 1. Thus, each of the following examples was prepared above formula and additive identified and in the amount as follows:

| Example | Additive | Amount |
|---|---|---|
| 1 | 4-aminoantipyrine | 6.8 mg |
| 2 | 3-hydroxy-2,4,6-triiodo benzoic acid | 17.26 mg |
| 3 | 3,5-di-tert-butyl-4-hydroxyanisole | 7.91 mg |
| 4 | sodium azide | 2.2 mg |
| 5 | N-ethyl-N-sulfopropyl-m-tolidine | 9.88 mg |
| 6 | 9-(3-aminopropyl)-3-amino carbazole | 10.72 mg |
| 7 (Control) | no additive | |

Test strips were prepared by submersing a Gelman Supor® 200 membrane (purchased from VWR Scientific) with the dye solution. After drying, the membranes were submersed in the enzyme solution After drying the second time, the membrane was cut into pieces 1 cm² and were ready for use. If desired, the coated membrane pieces can be mounted on a support to facilitate handling. The test strips were stored at room temperature in the presence of a silica gel drying agent. Calibration curves were prepared for the stressed test strips of each of the Examples and are illustrated, respectively, in FIGS. 1–7.

It can readily be seen that only the antipyrine compound provides the desired effect on linearity of the calibration curve (see FIG. 1).

Although the invention has been described in detail with reference to the preferred embodiments thereof, it will be appreciated by those skilled in the art, upon considering the present specification, that modifications and/or improvements may be made within the spirit and scope of the invention.

We claim:

1. A dry reagent test strip for determining the concentration of an analyte in a liquid sample, the test strip comprising a matrix containing reagent detection chemistry, the reagent detecting chemistry comprising: an oxidase enzyme that utilizes the analyte as a substrate forming hydrogen peroxide; a benzidine dye precursor; a peroxidase enzyme; and an antipyrine compound, wherein the antipyrine compound produces a standard curve of analyte concentration versus reflectance which is substantially linear in the desired range when the analyte contacts the reagent detecting chemistry.

2. The strip of claim 1, wherein the benzidine dye precursor is o-tolidine.

3. The strip of claim 1, wherein the benzidine dye precursor is o-tolidine HCl.

4. The strip of claim 1, wherein the benzidine dye precursor is a tetralkylbenzidine.

5. The strip of claim 4, wherein the benzidine dye precursor is a tetramethylbenzidine.

6. The strip of claim 1, wherein the antipyrine compound is an aminoantipyrine.

7. The strip of claim 6, wherein the aminoantipyrine is 4-aminoantipyrine.

8. A dry reagent test strip for determining the concentration of glucose in a sample of whole blood, the test strip comprising a matrix containing reagent detection chemistry, the reagent detecting chemistry comprising: glucose oxidase, a benzidine dye precursor, peroxidase and an antipyrine compound, wherein the antipyrine compound produces a standard curve of glucose concentration versus reflectance which is substantially linear in the desired range when the glucose contacts the reagent detecting chemistry.

9. The strip of claim 8, wherein the antipyrine compound is an aminoantipyrine.

10. The strip of claim 9, wherein the aminoantipyrine is 4-aminoantipyrine.

11. The strip of claim 8, wherein the benzidine dye precursor is o-tolidine.

12. The strip of claim 8, wherein the benzidine dye precursor is o-tolidine HCl.

13. The strip of claim 8, wherein the benzidine dye precursor is tetraalkylbenzidine.

14. The strip of claim 13, wherein the benzidine dye precursor is tetramethylbenzidine.

* * * * *